United States Patent
Yonezawa

(10) Patent No.: US 9,615,737 B2
(45) Date of Patent: Apr. 11, 2017

(54) IMAGE FORMING APPARATUS, IMAGE FORMING METHOD, PROGRAM, AND OPHTHALMIC APPARATUS

(71) Applicant: CANON KABUSHIKI KAISHA, Tokyo (JP)

(72) Inventor: Keiko Yonezawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 277 days.

(21) Appl. No.: 14/135,719

(22) Filed: Dec. 20, 2013

(65) Prior Publication Data

US 2014/0185006 A1 Jul. 3, 2014

(30) Foreign Application Priority Data

Dec. 28, 2012 (JP) ................................ 2012-288358

(51) Int. Cl.
*A61B 3/14* (2006.01)
*A61B 3/10* (2006.01)

(52) U.S. Cl.
CPC .............. *A61B 3/1025* (2013.01); *A61B 3/14* (2013.01)

(58) Field of Classification Search
CPC .. A61B 3/14; A61B 3/12; A61B 3/103; A61B 3/1015
USPC .................. 351/200, 205, 206, 246
See application file for complete search history.

(56) References Cited

U.S. PATENT DOCUMENTS

| | | | |
|---|---|---|---|
| 5,691,839 A | 11/1997 | Kobayashi | |
| 5,936,764 A | 8/1999 | Kobayashi | |
| 8,235,528 B2 | 8/2012 | Mukai et al. | |
| 8,699,774 B2 | 4/2014 | Yonezawa et al. | |
| 2010/0165291 A1* | 7/2010 | Sugita et al. | 351/206 |
| 2010/0277692 A1 | 11/2010 | Mukai et al. | |
| 2012/0320339 A1 | 12/2012 | Yonezawa | |
| 2012/0330140 A1 | 12/2012 | Yonezawa | |
| 2013/0058553 A1 | 3/2013 | Yonezawa et al. | |
| 2014/0119627 A1* | 5/2014 | Skretting et al. | 382/131 |

FOREIGN PATENT DOCUMENTS

| | | |
|---|---|---|
| JP | H06-300974 A | 10/1994 |
| JP | 2009-265285 A | 11/2009 |
| JP | 2010-259543 A | 11/2010 |

* cited by examiner

*Primary Examiner* — James Greece
(74) *Attorney, Agent, or Firm* — Fitzpatrick, Cella, Harper & Scinto

(57) ABSTRACT

A distortion in an image, which occurs when the image is formed by scanning a retina with a resonance scanner, is reduced. An image forming apparatus for forming an image of an object to be inspected includes: a detecting unit for detecting signals relating to a resonance scanner which is set to scan the object to be inspected with measurement light at a first frequency; a determining unit for determining a second frequency which is estimated to be used for the scanning by the resonance scanner, based on a correlation between groups of the detected signals for each cycle of the first frequency; and an image forming unit for forming the image of the object to be inspected based on the determined second frequency.

21 Claims, 11 Drawing Sheets

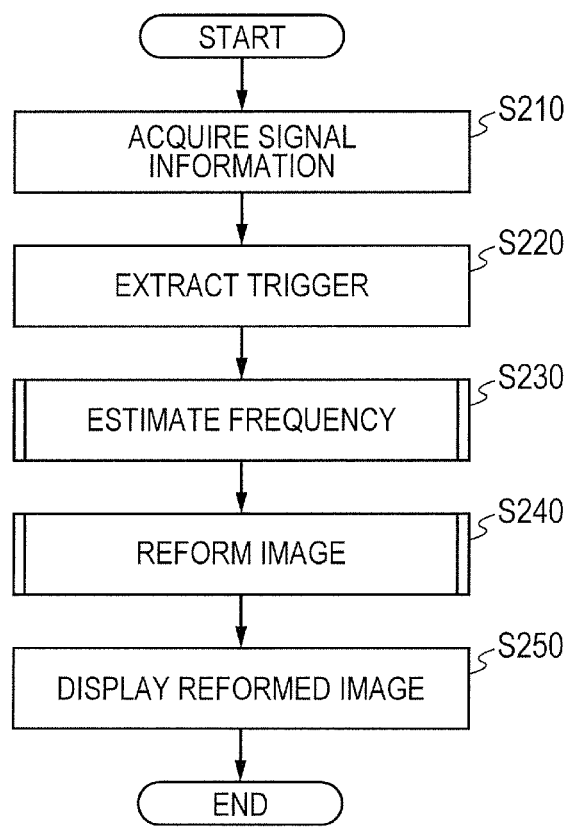

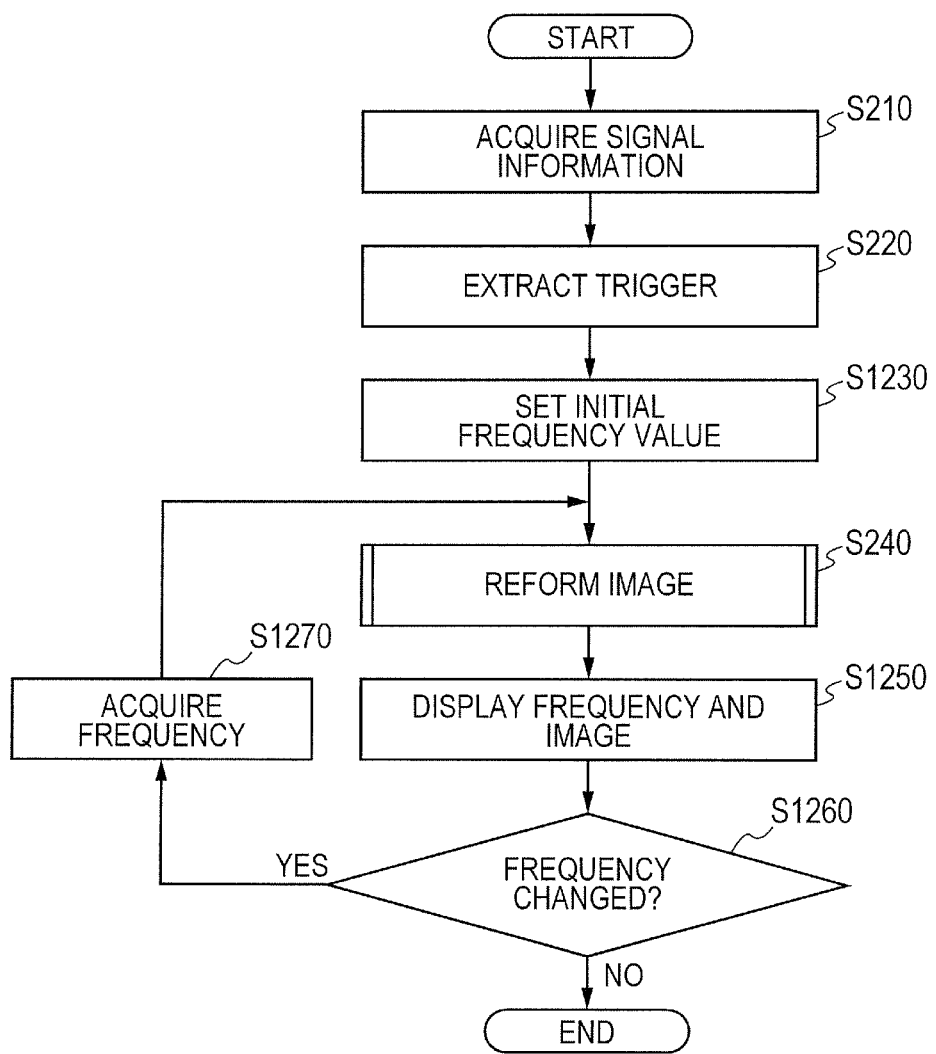

IMAGE FORMING APPARATUS, IMAGE FORMING METHOD, PROGRAM, AND OPHTHALMIC APPARATUS

BACKGROUND OF THE INVENTION

Field of the Invention

The present invention relates to an image forming apparatus and method, and more particularly, to an image forming apparatus and method used for an ophthalmic care and the like, a program, and an ophthalmic apparatus.

Description of the Related Art

An examination of a fundus of an eye is widely performed for the purpose of a diagnosis in early stage of a disease that usually ranks high in adult disease or cause of blindness. A scanning laser ophthalmoscope (SLO) which uses a principle of a confocal laser microscope is an ophthalmic apparatus that performs a raster scanning on a fundus of an eye with laser light which is measurement light and acquires a two-dimensional image of the fundus of the eye from return light with a high resolution at a high speed. In recent years, an adaptive optics SLO has been developed which includes an adaptive optical system for measuring an aberration of an eye to be inspected in real time with a wavefront sensor and correcting the aberrations of measurement light and return light generated at the eye to be inspected with a wavefront correction device, enabling an acquisition of a two-dimensional image with a high lateral resolution (Japanese Patent Application Laid-Open No. 2010-259543).

With the SLO described above, the image of the eye to be inspected can be obtained by setting a value of a signal acquired by a resonance scanner which is capable of performing high-speed scanning to a value of a pixel corresponding to a position of the scanner at the time when the signal is acquired. A frequency of the resonance scanner changes with time due to a temperature or the like, and therefore does not become constant. As a result, a distortion disadvantageously occurs in the formed image.

SUMMARY OF THE INVENTION

In view of the problem described above, the present invention is to reduce a distortion in an image, which occurs when the image is formed by scanning a retina with a resonance scanner.

In order to solve the above-mentioned problem, according to one aspect of the present invention, there is provided an image forming apparatus for forming an image of an object to be inspected, including: a detecting unit for detecting signals relating to a resonance scanner which is set to scan the object to be inspected with measurement light at a high frequency; a determining unit for determining a second frequency which is estimated to be used for the scanning by the resonance scanner, based on a correlation between groups of the detected signals for each cycle of the first frequency; and an image forming unit for forming the image of the object to be inspected based on the determined second frequency.

Further, according to another aspect of the present invention, there is provided an image forming method for forming an image of an object to be inspected, including: detecting signals relating to a resonance scanner which is set to scan the object to be inspected with measurement light at a first frequency; determining a second frequency which is estimated to be used for the scanning by the resonance scanner, based on a correlation between groups of the detected signals for each cycle of the first frequency; and forming the image of the object to be inspected based on the determined second frequency.

According to the present invention, based on the correlation between the signal groups relating to the resonance scanner, which are detected for each cycle of the first frequency set for the resonance scanner, the second frequency, which is estimated as having been (actually) used for the scanning by the resonance scanner, can be determined. In this manner, the distortion of the image, which occurs when the image is formed by scanning the retina with the resonance scanner, can be reduced.

Further features of the present invention will become apparent from the following description of exemplary embodiments with reference to the attached drawings.

BRIEF DESCRIPTION OF THE DRAWINGS

FIG. 2 is a flowchart illustrating a processing procedure of the image forming apparatus according to the first embodiment.

FIG. 12 is a flowchart illustrating a processing procedure of the image forming apparatus according to the second embodiment.

DESCRIPTION OF THE EMBODIMENTS

First Embodiment

In a first embodiment of the present invention, there is described processing for reforming an image based on signal values obtained by the combination of a resonance scanner and a galvano scanner when an image of a retina photographed by an adaptive optics SLO is to be acquired. Specifically, a group of trigger signals for the galvano scanner (hereinafter referred to as "galvano triggers"), which corresponds to one image, and a group of trigger signals for the resonance scanner (hereinafter referred to as "resonance triggers"), which corresponds to two vertical reciprocation lines of the image, are acquired. By using the trigger signals, a frequency of the resonance scanner for the one image is estimated as a frequency which minimizes a variation between positions at which the trigger signals for the resonance scanner are acquired. Based on the estimated frequency, a correction for a reform start position and a sine correction are performed to reform the image. By reforming the image in this manner, the retina image whose distortion caused by the resonance scanner is corrected can be acquired at a high speed.

There is known a method of acquiring and controlling the position of scanning with the scanner by using hardware. Besides, according to a technique called "pixel clock", there is known a mechanism of performing control so that only the signals located at the positions corresponding to pixels of the image are acquired. With the method using the hardware, however, there is a possibility that cost for manufacturing the apparatus may be increased. Specifically, a size of the apparatus is affected, design is limited, or a radio field intensity generated from the apparatus is varied. In the first embodiment, the retina image whose distortion caused by the resonance scanner is corrected can be acquired at a high speed without using special hardware.

(Configuration of Image Forming Apparatus)

Figure 1:
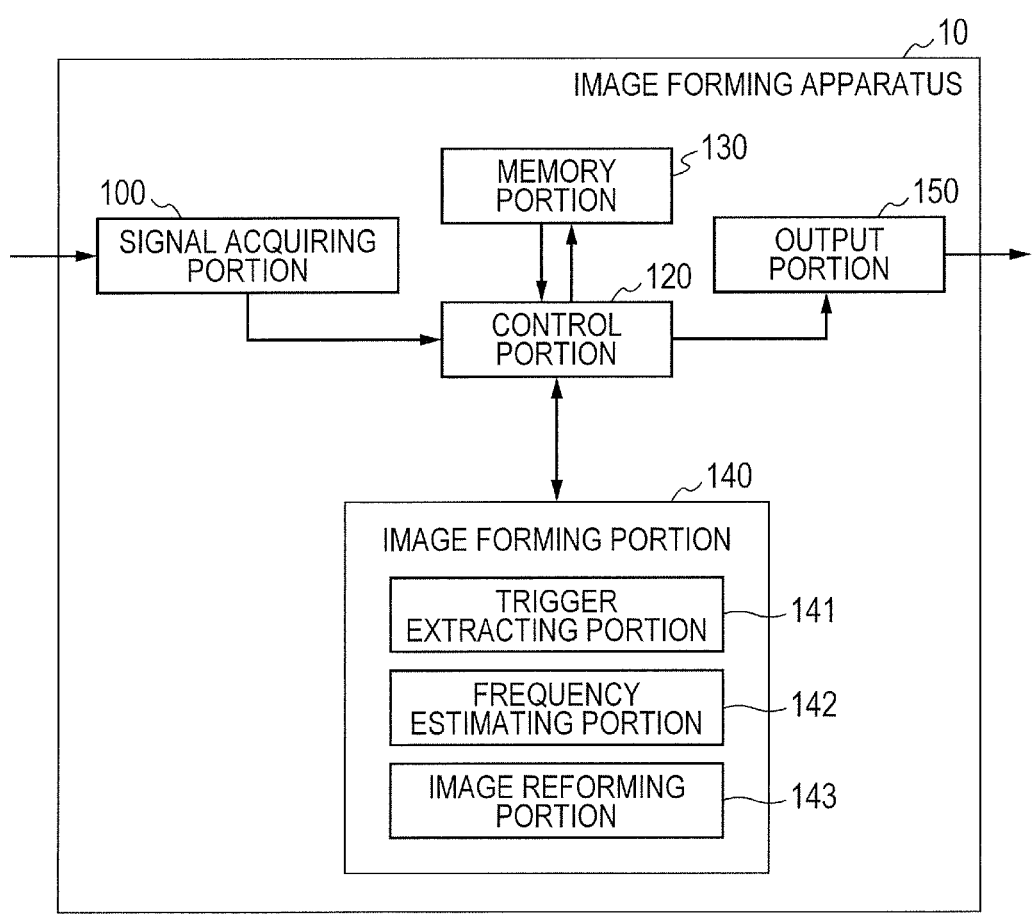
FIG. 1 is a diagram illustrating a functional configuration of an image forming apparatus according to a first embodiment of the present invention.

FIG. 1 illustrates a functional configuration of an image forming apparatus 10 according to the first embodiment.

FIG. 1 illustrates a signal acquiring portion 100, a control portion 120, a memory portion 130, an image forming portion 140, and an output portion 150. The signal acquiring portion 100 acquires the trigger signal for the resonance scanner and the trigger signal for the galvano scanner from the adaptive optics SLO apparatus and a reflected signal from the retina. The acquired information is stored in the memory portion 130 through the control portion 120. The image forming portion 140 includes a trigger extracting portion (trigger detecting unit) 141, a frequency estimating portion 142, and an image reforming portion 143. The image forming portion 140 extracts or detects the trigger signals for the galvano scanner and the resonance scanner from the acquired signals, and quantifies a variation between the positions at which the extracted trigger signals are detected, by using a correlation coefficient, thereby minimizing the variation. In this manner, a frequency of the resonance scanner is estimated. Then, based on the estimated frequency, the image of the retina is reformed. The output portion 150 outputs the formed image to a monitor or the like.

(Processing Procedure of Image Forming Apparatus)

Next, a processing procedure of the image forming apparatus 10 according to the first embodiment is described referring to a flowchart of FIG. 2.

(Step S210)

In Step S210, the signal acquiring portion 100 acquires signal information acquired from the adaptive optics SLO connected to the image forming apparatus 10. In this case, the signal information is the trigger signals for the galvano scanner and the resonance scanner, which are used to photograph the retina, and an optical signal which is reflected light of measurement light from the retina, which is acquired by the photographing, that is, a reflected signal. The acquired signal information is stored in the memory portion 130 through the control portion 120.

Control information for the hardware, which is associated with the acquired signal information, is also acquired, and is stored in the memory portion 130 through the control portion 120. In this case, the control information is a frame rate corresponding to a sampling frequency or a frequency of the galvano scanner, which is obtained when the reflected signal of the retina is acquired. The control information described above is written in a photography-information file included in the signal information in some cases or is contained as tag information of the signal information in other cases.

(Step S220)

In Step S220, the trigger extracting portion 141 acquires positions of the trigger signals for the galvano scanner and the trigger signals for the resonance scanner from the signal information stored in the memory portion 130, which is acquired by the adaptive optics SLO. The thus extracted trigger positions are stored in the memory portion 130 through the control portion 120. The trigger positions are described later.

Figure 3A:
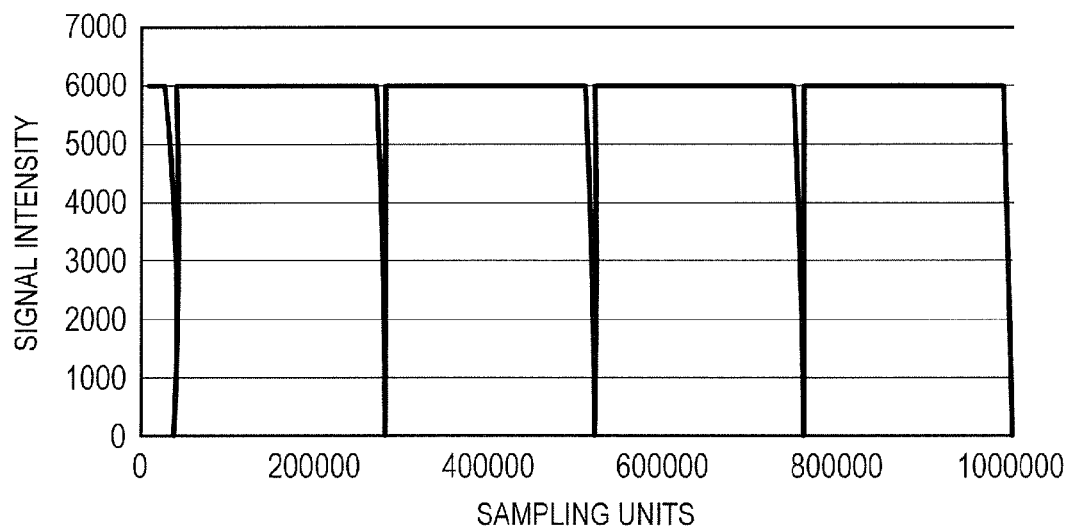
FIG. 3A is a graph schematically showing trigger signals for a galvano scanner.
Figure 3B:
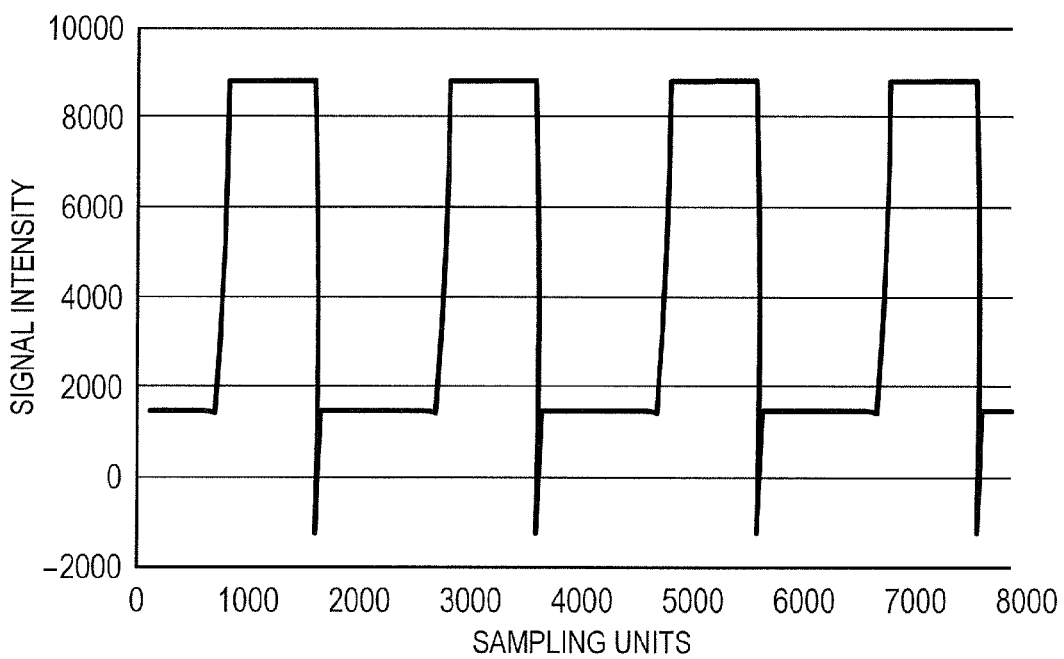
FIG. 3B is a graph schematically showing trigger signals for a resonance scanner.

FIG. 3A is a graph schematically showing the trigger signals for the galvano scanner, whereas FIG. 3B is a graph schematically showing the trigger signals for the resonance scanner. The galvano scanner oscillates measurement light in a specified cycle and a specified waveform to perform scanning with the measurement light. The galvano scanner outputs a specific signal, for example, whose output value becomes 0 V, at predetermined timing of the oscillating waveform. In the schematic graph of FIG. 3A, timing at which a signal intensity becomes zero corresponds to the output of the specific signal. The output of the specific signal is referred to as "trigger" because the output is a "trigger" of the start or end of one unit operation. Therefore, the acquired signal is referred to as "trigger signal". The resonance scanner oscillates at an oscillating speed along, for example, a sine waveform, and its output signal changes at two levels in accordance with a change of a direction of movement. An output at the time of inversion is referred to as "trigger" in the resonance scanner, and the acquired signal is referred to as "trigger signal" as in the case of the galvano scanner. In this case, the trigger for the galvano scanner corresponds to one image, whereas the trigger for the resonance scanner corresponds to two lines (reciprocation lines) in one image. The horizontal axis indicates one sampling as one unit. However, the sampling is actually performed at 15 MHz. Therefore, 15 M corresponds to one second.

More specifically, the signals are as shown in FIGS. 3A and 3B. Therefore, the triggers are extracted by threshold-value processing. Specifically, in the case of the galvano scanner, when a change of the intensity of the output signal described above becomes lower than a given threshold value (set to 2,000 in this case), the signal is detected as the trigger signal. On the other hand, in the case of the resonance scanner, a change of the level of a driving voltage from High to Low or Low to High is detected as the generation of the trigger signal. Alternatively, when a change of the intensity of the output signal described above becomes equal to or higher than a given threshold value (set to 3,000 in this case), the signal may be detected as the trigger signal. In this embodiment, the change of the level of the signal intensity to the threshold value or higher is detected by the function of the trigger extracting portion 141 as a detection unit for the resonance trigger signal. The generation of the trigger signal is determined based on the detection of the change described above. Specifically, the resonance scanner is set so as to scan an object to be inspected by the measurement light at a first frequency. The detection unit detects the driving voltages as signals relating to the resonance scanner.

In the example shown in FIGS. 3A and 3B, the trigger of the galvano scanner is detected at the positions of 40,000, 280,000, 520,000, and 760,000 in sampling units, whereas the trigger of the resonance scanner is detected at the positions of, that is, sampling timing of 700, 2,700, 4,700, and 6,700. The sampling at the sampling timing shown in FIGS. 3A and 3B indicates a time period required to acquire the image information or a time at which the acquisition of the image information is started. For example, in the galvano scanner, in a stage (at timing) of acquisition of 40,000 pieces of the image information as the sampling timing, the trigger signal is extracted. The unit "1" indicated on the horizontal axis of FIGS. 3A and 3B shown in this embodiment corresponds to $1/15$ milliseconds in terms of time. In FIGS. 3A and 3B, the trigger position is understood as sampling timing in accordance with the number of times of acquisition of the image information. Specifically, the sampling timing is understood as timing defined in one arbitrary time unit when a time period required for the sampling of one piece of the image information is assumed as one arbitrary time unit. The sampling timing can be understood as a mode of the timing. Similarly to the case of the galvano scanner, the trigger position detected by the resonance scanner means detection timing of the trigger signal when the sampling timing is used as a time axis.

In this case, various methods are conceivable as a method of acquiring the trigger position. For example, a method of setting a maximum value output from the galvano scanner as the trigger signal and setting the position of extraction of the maximum value as the trigger position may be used. Therefore, the method of acquiring the trigger position is not limited to the technique described above.

(Step S230)

In Step S230, the frequency estimating portion 142 estimates the frequency of the resonance scanner based on the trigger positions acquired in Step S220, that is, the sampling timings. The thus estimated frequency is stored in the memory portion 130 through the control portion 120. In this case, the frequency estimating portion 142 functions as a determination unit for determining a second frequency which is estimated to be used for the actual scanning by the resonance scanner with the measurement light in the present invention. The determination unit determines the second frequency based on the groups of the signals detected for each cycle of a frequency $f_0$, that is, the correlation between the signal groups.

Figure 4:
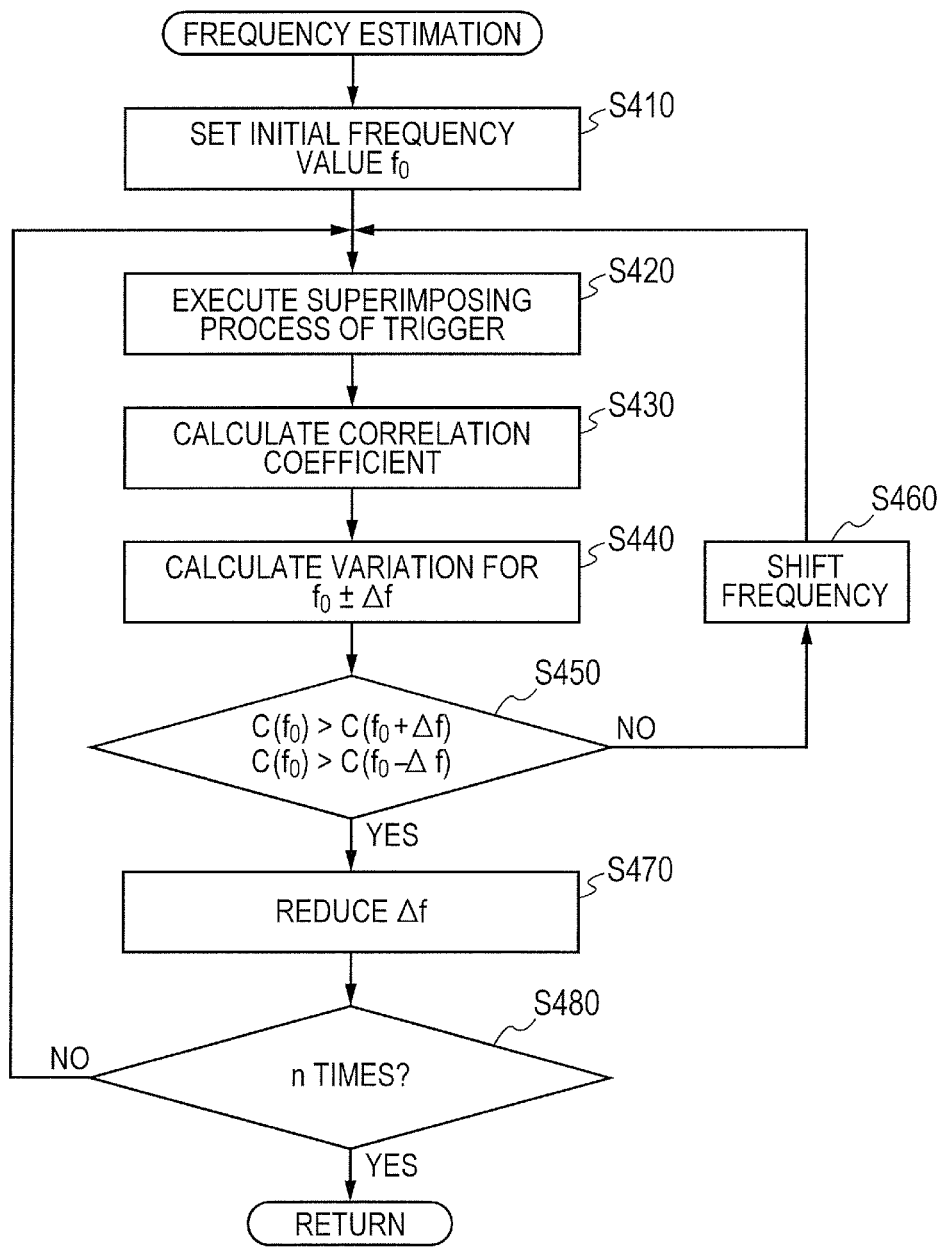
FIG. 4 is a flowchart specifically illustrating frequency estimation illustrated in FIG. 2.

FIG. 4 illustrates a flowchart for specifically illustrating the estimation of the frequency.

(Step S410)

In Step S410, the frequency estimating portion 142 sets the initial value f0 of the frequency of the resonance scanner as a set frequency which is the first frequency in the present invention, based on the control information acquired in Step S210. There exist several methods as the method of setting the initial value. For example, when an average driving frequency is output from the resonance scanner, a value of the average driving frequency may be used. The number of the trigger signals for the resonance scanner, which are contained during the sampling for one image illustrated in FIGS. 3A and 3B, may be acquired to be approximated. In this case, the initial frequency $f_0$ is set to 7,923 Hz.

(Step S420)

In Step S420, the frequency estimating portion 142 performs superimposing process on the triggers based on the frequency $f_0$ set in Step S410. In the first embodiment, the signal acquired from the galvano scanner, which is actually used in the SLO apparatus as the trigger signal to be superimposed, is used as a second trigger signal. However, a configuration from which the second trigger signal is acquired is not limited to the galvano scanner as long as an appropriate trigger signal is acquired as the second trigger signal to be superimposed.

Figure 5:
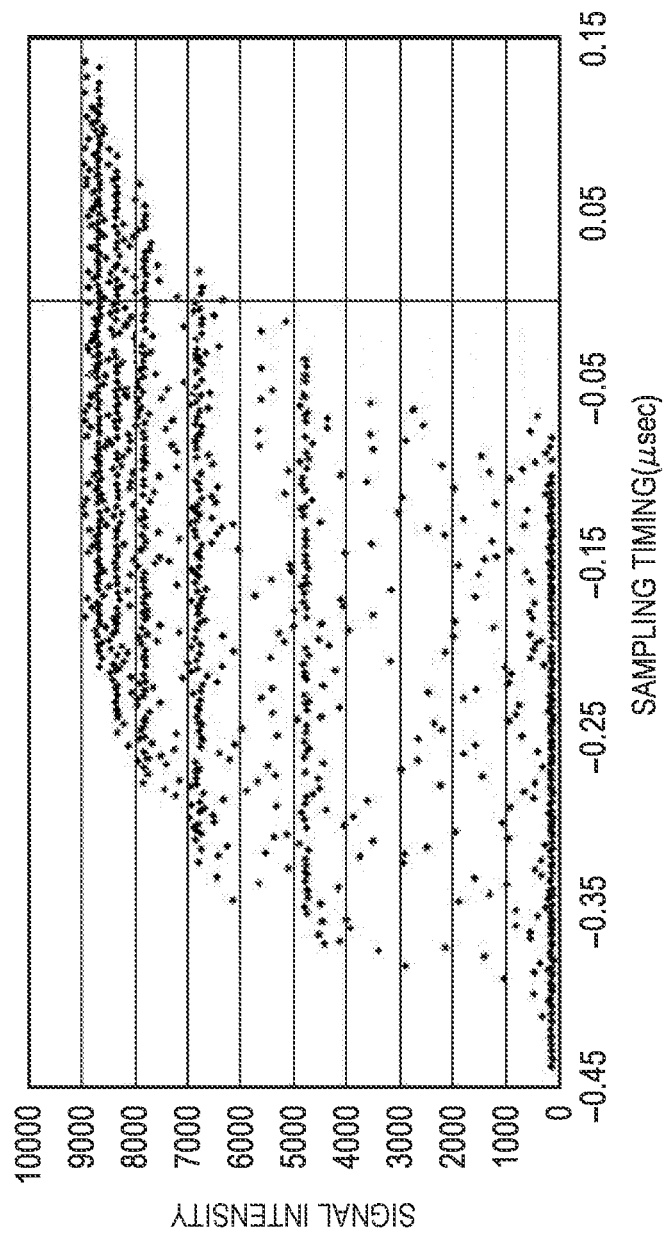
FIG. 5 is a graph showing an example of superimposing display of a trigger signal.

Specifically, by using an arbitrary trigger position in the trigger signal acquired from the galvano scanner in Step S220 as a center, intensity values of the trigger signals acquired from the resonance scanner, which are located around the trigger position, are shifted by a cycle $T_0=1/f_0$. Then, the signals for one image are superimposed. FIG. 5 shows an example of the thus created superimposing display (hereinafter processing for superimposing the trigger signals with a shift by a resonance cycle of the estimation for the resonance scanner is referred to as "superimposing process" for the trigger signals, and the thus created image shown in FIG. 5 is referred to as "superimposing display" of the trigger signals). In this case, about 200 signal intensities at four sampling points in total, that is, at a sampling point acquired as the arbitrary trigger position of the trigger signals acquired from the galvano scanner, and one sampling position before and two sampling points after the above-mentioned sampling point are collected for one image. Then, after being shifted by the cycle $T_0$, the signal intensities are plotted as shown in FIG. 5. Reflecting the sampling performed at 15 MHz, the X axis is indicated in time (psec).

The determination of the second frequency is described in relation to the actual resonance scanner. A correlation coefficient is calculated by a correlation coefficient calculating unit through the superimposing process of the intensities of the signal group, which are acquired corresponding to a time at which the resonance scanner is located at a first position, that is, a first rotation angle and the superimposing process of the intensities of the signal group, which are acquired corresponding to a time at which the resonance scanner is located at a second position which is different from the first position, that is, a second rotation angle, based on the frequency $f_0$. A frequency at which a variation between the positions of detection of the signal group, which are exemplified by the correlation coefficient obtained by the above-mentioned calculation, that is, a variation between the rotation angles specified by the signals, falls within or becomes smaller than a predetermined range, at which the correlation coefficient becomes equal to or larger than a predetermined value, is determined as a central frequency described later or the second frequency of the present invention.

If the trigger signals are perfectly periodic and the frequency $f_0$ is identical with a frequency of the trigger signals, the signal intensities are plotted in a superimposed manner on a single straight line of the signal intensity obtained by superimposing the trigger signals. Specifically, the variation between the signal intensities described in this case corresponds to a variation between the periods of the trigger signals, that is, a variation between the trigger positions or the positions of detection at the sampling timings. The variation between the periods of the trigger signals also corresponds to a variation in the operation of the resonance scanner or a variation between rotation cycles.

(Step S430)

In Step S430, the frequency estimating portion 142 calculates the correlation coefficient based on the superimposing process performed in Step S420. More specifically, when estimating the central frequency described below as a frequency estimating unit, the frequency estimating portion 142 superimposes the trigger signal acquired from the resonance scanner and the second trigger signal acquired from the galvano scanner, which is different from the trigger signal described above, based on the set frequency set for the trigger signal. Then, based on the result of superimposition, the correlation coefficient is calculated. The above-mentioned step is carried out in a region which functions as a correlation-coefficient calculating portion in the frequency estimating portion 142. Specifically, the correlation between the multiple trigger signals is obtained by the superimposing process.

In this case, the correlation coefficient is calculated to quantitatively evaluate a magnitude of the variation obtained by the superimposing process. Specifically, in an ideal case of the superimposing display, the correlation coefficient is calculated to acquire a quantitative index which indicates a small variation when all the plotted points are located on the single straight line and indicates a large variation when the plotted points are distributed over a certain range as shown in FIG. 5.

As the correlation coefficient, a Pearson's product-moment correlation coefficient or a Spearman's rank correlation coefficient can be used. In this case, the Pearson's product-moment correlation coefficient with which the processing becomes simpler is used.

Assuming that the sampling point indicated by the superimposing display of the triggers shown in FIG. 5 is X (in psec) and the signal intensity is Y, the following Pearson's product-moment correlation coefficient is calculated.

$$\text{coefficient(Pearson)} = \frac{\sum xy - \sum x \sum y}{\sqrt{\sum x^2 - (\sum x)^2} \sqrt{\sum y^2 - (\sum y)^2}}$$

Figure 6:
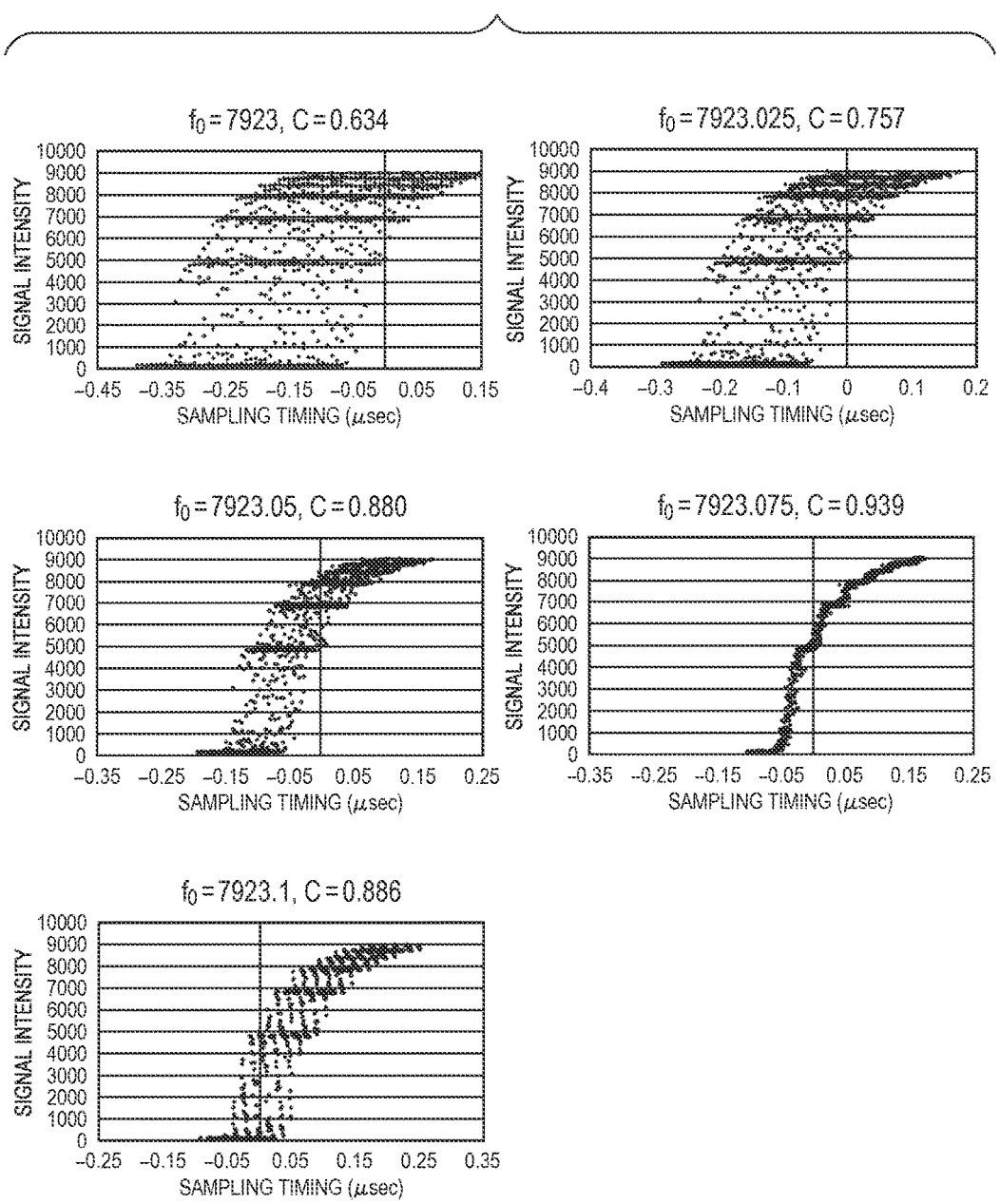
FIG. 6 is a graph showing the relationship between a variation between the trigger signals, the frequency, and a correlation coefficient.
Figure 7:
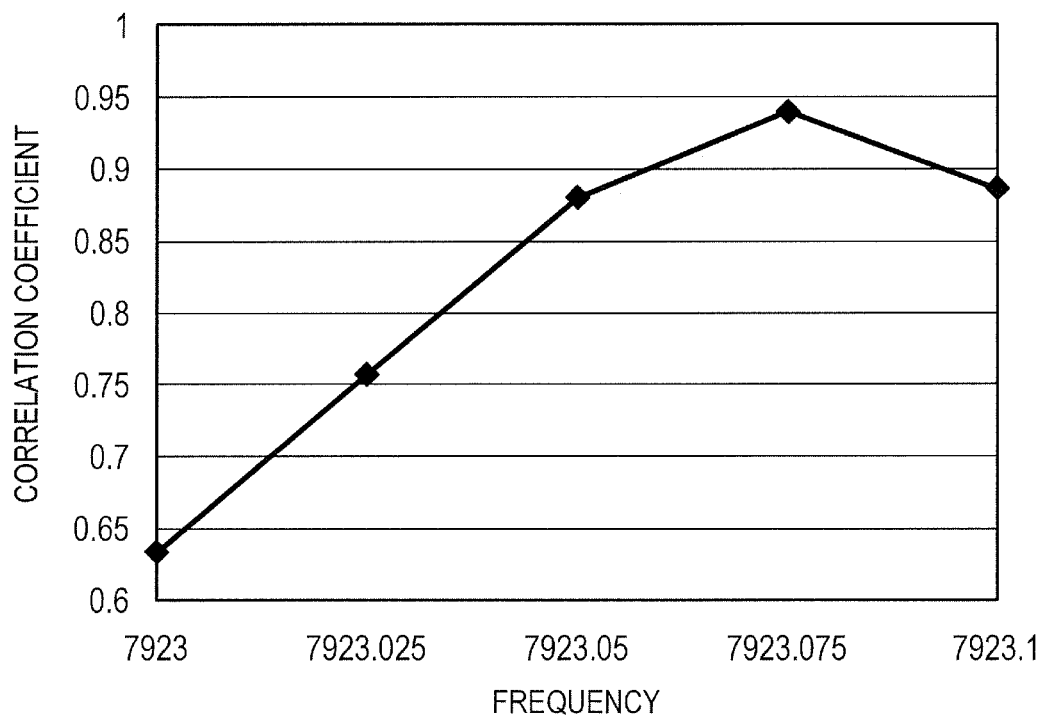
FIG. 7 is a graph showing the relationship between the frequency and the correlation coefficient.

FIG. 6 shows the results of the superimposing process of the trigger signals acquired from the resonance scanner and the correlation coefficients when the variation is changed by varying the initial value of the frequency. Further, FIG. 7 shows the relationship between the frequency and the correlation coefficient. As shown in FIGS. 6 and 7, when the value of the frequency is varied, the variation between the signal intensities of the trigger signals shown on the superimposing display changes with the variation of the value of the frequency. Thus, FIGS. 6 and 7 show that the Pearson's correlation coefficient can be used as the quantitative index of the variation. As the variation becomes larger, the value of the correlation coefficient becomes smaller.

(Step S440)

In Step S440, the frequency estimating portion 142 calculates the variations for the frequencies shifted by ±Δf from the frequency set in Step S410. Specifically, the superimposing process of the triggers is performed for the frequencies $f_0+\Delta f$ and $f_0-\Delta f$ to calculate the correlation coefficients for the respective frequencies. Although a magnitude of Δf depends on the characteristics of the resonance scanner and the range of the frequency which is desired to be examined, the magnitude of Δf is set to 0.1 Hz in this case.

(Step S450)

In Step S450, the frequency estimating portion 142 determines whether or not the values of the correlation coefficients for the frequencies $f_0+\Delta f$, $f_0$, and $f_0-\Delta f$, which are obtained in Step S440, satisfy the following relationships. In this case, the value of the correlation coefficient for the frequency $f_0$ is $C(f_0)$.

$C(f_0) > C(f_0 - \Delta f)$ $C(f_0) > C(f_0 + \Delta f)$

When the relationships described above are satisfied, the processing proceeds to Step S470. On the other hand, when the relationships are not satisfied, the processing proceeds to Step S460. The relationships described above are satisfied in the case where the frequency at which the correlation coefficient becomes the largest, that is, the variation becomes the smallest, is contained in the range between $f_0-\Delta f$ and $f_0+\Delta f$. In such a case, processing for obtaining a frequency with higher accuracy is performed in Step S470. On the other hand, when there is a possibility that the frequency at which the variation becomes the smallest is not contained in the range between $f_0-\Delta f$ and $f_0+\Delta f$, the range in which the frequency is searched for is changed in Step S460.

(Step S460)

In Step S460, the frequency estimating portion 142 shifts the range in which the frequency allowing the variation between the results of the superimposing process of the signal intensities of the trigger signals to become the smallest is searched for by Δf. Specifically, in the case of: $C(f_0-\Delta f) > C(f_0+\Delta f)$, $f_0-\Delta f$ is set as the initial value of the frequency. Then, the processing returns to Step S420. In the case of: $C(f_0+\Delta f) > C(f_0-\Delta f)$, $f_0+\Delta f$ is set as the initial value of the frequency. Then, the processing returns to Step S420.

(Step S470)

In Step S470, the frequency estimating portion 142 limits the range in which the frequency at which the variation between the results of the superimposing process of the triggers becomes the smallest is searched for to a range of ±Δf/2 having $f_0$, $f_0-\Delta f/2$, or $f_0+\Delta f/2$ as the central frequency. Specifically, the processing corresponds to the reduction of the value of Δf to half. In this step, as the central frequency, the frequency at which the correlation coefficient becomes the largest is selected. Specifically, the central frequency at which the variation between the positions of the extracted trigger signals falls within the predetermined range or becomes smaller is estimated as the frequency of the resonance scanner. The above-mentioned processing is performed by selecting the set frequency at which the correlation coefficient calculated by the above-mentioned correlation coefficient calculating portion which is a correlation coefficient calculating unit becomes equal to or larger than a predetermined value as the central frequency. The central frequency is selected by a region of the frequency estimating portion 142, which functions as a central-frequency selecting unit.

By repeating the processing in Step S470, the accuracy of the estimate value of the frequency at which the variation between the results of superimposing process becomes small can be improved. Specifically, by repeating the processing for N times, the estimation accuracy of the frequency becomes $\pm\Delta f/2^N$. Thus, the number of repeat times is determined in accordance with the desired accuracy. In this case, N=3 is set.

(Step S480)

In Step S480, the frequency estimating portion 142 determines how many times the processing in Step S470 has been repeated. When the number of repeat times is smaller than N, the processing returns to Step S420 after Δf=Δf/2 is set. When the number of repeat times becomes equal to or larger than N, the processing returns to Step S230 after the central frequency acquired at the time is set as the estimate value of the frequency. The estimate value of the central frequency described above is determined in the region of the image forming portion 140 including the frequency estimating portion 142, which functions as a frequency estimating portion. The processing repeated for N times is an exemplification of the processing defined as predetermined processing in the present invention, and corresponds to processing for evaluating the variation between the trigger signals extracted using the correlation coefficient to determine the frequency of the resonance scanner in this embodiment.

As described above, in Step S230, based on the sampling timings which are the positions of the trigger signals extracted or detected by the trigger extracting portion 141, that is, the trigger detecting portion, the frequency of the resonance scanner is determined. The operation described above is performed by the region of the image forming portion 140, which functions as a frequency determining unit.

(Step S240)

In Step S240, the image reforming portion 143 which is an image reforming unit reforms the image based on the value of the frequency acquired in Step S230. Then, the reformed image of the retina obtained by the adaptive optics SLO is stored in the memory portion 130 through the control portion 120.

In this step, simultaneously with the sine correction for the movement of the resonance scanner, a shift from a design value of the reform start position is corrected.

Figure 8:
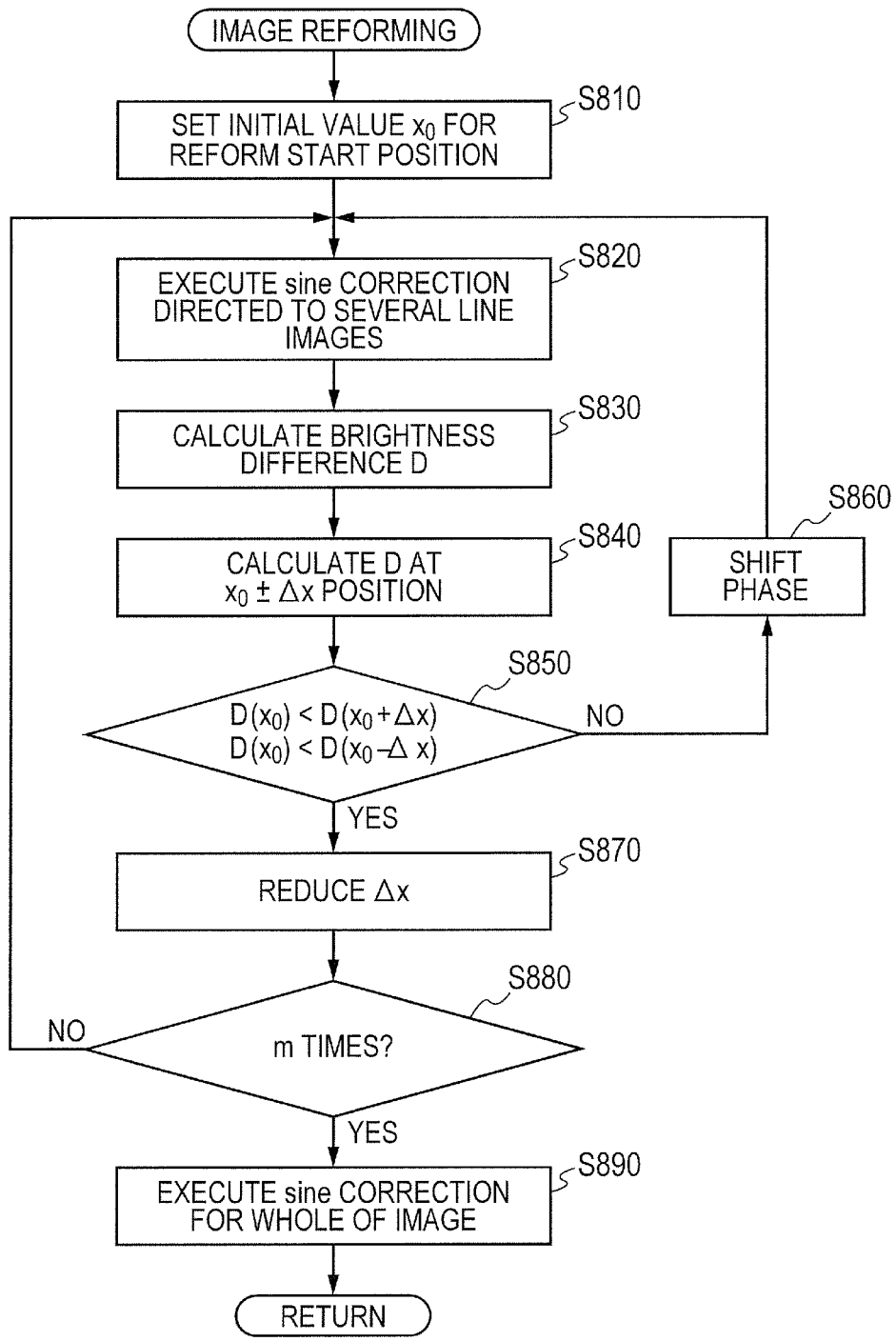
FIG. 8 is a flowchart specifically illustrating image reformation illustrated in FIG. 2.

FIG. 8 is a flowchart for specifically illustrating the image reformation.

The image reformation described below is performed for each one of multiple images which are photographed sequentially. Specifically, the following processing is performed for one image corresponding to each one of the trigger signals for the galvano scanner, which are acquired in Step S220. The processing is repeated for the number of times corresponding to the number of images. After the image reformation is performed for all the images, an image group obtained by integrating the reformed images is formed. Then, the thus formed image group is stored in the memory portion 130.

(Step S810)

In Step S810, the image reforming portion 143 sets the design value of the reform start position, which is provided from the control information acquired in Step S210 as an initial value $x_0$ of the reform start position. For example, the design value is acquired by subtracting a delay amount of the trigger from the trigger position at 432 sampling points.

(Step S820)

In Step S820, the image reforming portion 143 performs the sine correction directed to several lines of the image based on the reform start position $x_0$ set in Step S810.

Figure 10:
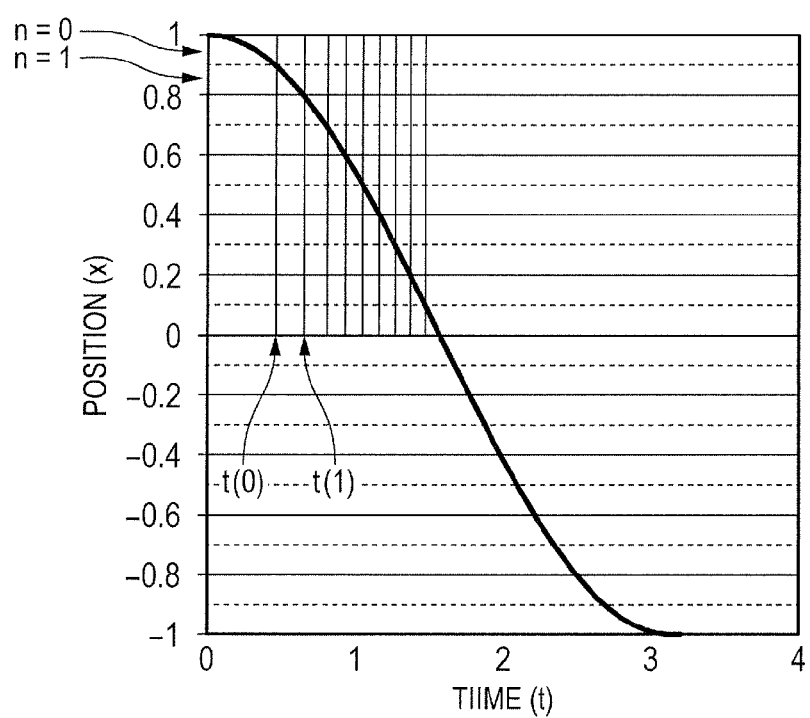
FIG. 10 is a graph for showing sine correction.

FIG. 10 is a graph schematically showing the sine correction. The sampling is performed at 15 MHz and at equal time intervals. It is assumed that a corresponding position of the scanner is a position corresponding to a sine wave of the frequency acquired in Step S230. Therefore, a brightness value of the obtained reflected signal is associated with a pixel value at the corresponding position. When multiple signals correspond to one pixel, an average value of the multiple signals is acquired as the pixel value.

The above-mentioned operation is performed by a region of the image reforming portion 143, which functions as a position associating portion. More specifically, the above-mentioned operation is performed by individual pixels which receive the reflected signal. Light receiving portions which are multiple light-receiving units which respectively generate the signals to be acquired by the resonance scanner are included in the signal acquiring portion 100. The position associating portion which is a position associating unit associates the positions on an eye to be inspected at which the signals are acquired by the resonance scanner and the positions of the multiple light-receiving elements based on the frequency of the resonance scanner determined by the frequency determining portion described above.

In this case, instead of forming the whole image, only several lines from the start of the image are formed. Specifically, when an image size is 400×400 pixels and the scanning is performed in a vertical direction from the upper right by the resonance scanner, the formation of several lines from the start of the image corresponds to the formation of an elongated image of n×400 pixels for n lines from the right. The thus generated n×400 pixel image is referred to as "line image". As the value of n increases, processing accuracy is enhanced. However, processing time becomes longer. In this case, n=20 is set. Specifically, the image reforming portion 143 also includes a region which functions as a line-image forming unit for forming a linear image based on the signal intensities respectively obtained from the pixels associated by the position associating portion described above. In this embodiment, an example where the image is immediately formed based on the obtained signal intensities is described. In another mode, however, the obtained signal intensities may be temporarily stored as data, and desired data may be read out as needed to form the image.

(Step S830)

In Step S830, the image reforming portion 143 calculates a brightness difference D based on the pixel values of the line image formed in Step S820. In this case, the brightness difference D is the sum of absolute values of differences of the brightness values of the horizontally adjacent pixels in the line image.

Figure 9A:
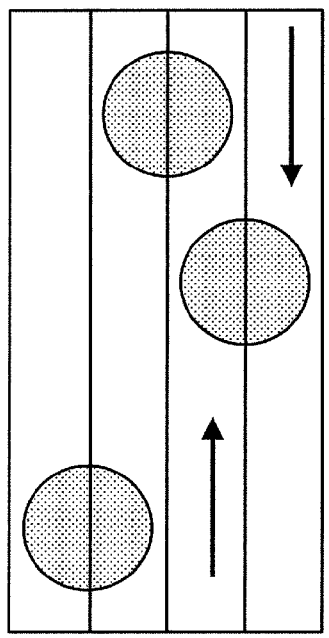
FIGS. 9A and 9B are schematic diagrams illustrating the influence of a shift of a reform start point on an image.
Figure 9B:
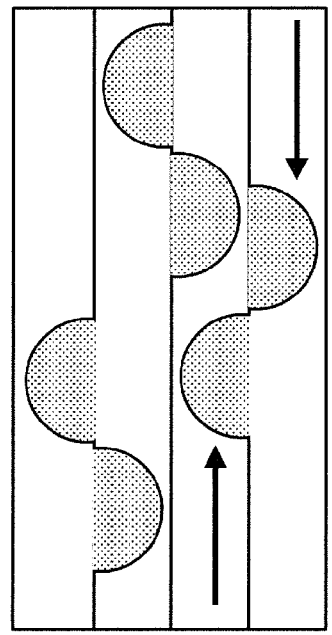

The brightness difference D is calculated to quantitatively evaluate the deterioration of image quality, which is caused by a shift of the reform start position. Specifically, in the case where the reform start position is correctly set as illustrated in FIG. 9A, the brightness differences between the horizontally adjacent pixels are small. On the other hand, in the case where the reform start position is shifted as illustrated in FIG. 9B, the brightness differences between the horizontally adjacent pixels are large.

(Step S840)

In Step S840, the image reforming portion 143 calculates the brightness difference D for the reform start position shifted from the reform start position set in Step S810 by $\pm\Delta x$. Specifically, the line images are formed by using $x_0+\Delta x$ and $x_0-\Delta x$ as the reform start positions. Then, the brightness differences D are calculated for the respective line images. Although depending on a resolution of the image or a scanning rate, the magnitude of $\Delta x$ is set to one sampling unit.

(Step S850)

In Step S850, the image reforming portion 143 determines whether or not the brightness differences of the line images with the reform start positions $x_0+\Delta x$, $x_0$, and $x_0-\Delta x$, which are obtained in Step S840, satisfy the following relationships. In this case, a value of the brightness difference corresponding to the reform start position $x_0$ is $D(x_0)$.

$$D(x_0) < D(x_0 - \Delta x)$$

$$D(x_0) < D(x_0 + \Delta x)$$

When the relationships described above are satisfied, the processing proceeds to Step S870. When the relationships are not satisfied, the processing proceeds to Step S860. The relationships described above are satisfied in the case where the reform start position with which the brightness difference becomes the smallest lies between $x_0-\Delta x$ and $x_0+\Delta x$. In such a case, processing for obtaining the reform start position with higher accuracy is performed in Step S870. On the other hand, when there is a possibility that the reform start position with which the brightness difference becomes the smallest does not lie between $x_0-\Delta x$ and $x_0+\Delta x$, the range in which the reform start position is searched for is changed in Step S860.

(Step S860)

In Step S860, the image reforming portion 143 shifts the range in which the reform start position allowing the brightness difference of the line image to become the smallest is searched for by $\Delta x$. Specifically, when the relationship: $D(x_0-\Delta x) > D(x_0+\Delta x)$ is satisfied, $x_0+\Delta x$ is set as the initial value of the reform start position. Then, the processing returns to Step S820. On the other hand, when the relationship: $D(x_0+\Delta x) > D(x_0-\Delta x)$ is satisfied, $x_0-\Delta x$ is set as the initial value of the reform start position. Then, the processing returns to Step S820.

(Step S870)

In Step S870, the image reforming portion 143 limits the range in which the image restart position allowing the brightness difference of the line image to become the smallest is searched for to the range $\pm \Delta x/2$ from the reform start position $x_0$, $x_0-\Delta x/2$, or $x_0+\Delta x/2$ as the center. Specifically, the processing in this step corresponds to the reduction of the value of $\Delta x$ to half. The reform start position as the center is selected so that the brightness difference becomes the smallest.

By repeating the processing in Step S870, the accuracy of the reform start position with a small brightness difference can be improved. Specifically, by repeating the processing for M times, the accuracy of estimation of the reform start position becomes $\pm \Delta x/2^M$. The number of repeat times is determined in accordance with desired accuracy. In this case, M=3 is set.

(Step S880)

In Step S880, the image reforming portion 143 determines how many times the processing in Step S870 has been repeated. When the number of repeat times is smaller than M, $\Delta x=\Delta x/2$ is set. Then, the processing returns to Step S820. When the number of repeat times is M or larger, the reform start position at the time when the number of repeat times is M is acquired.

(Step S890)

In Step S890, the image reforming portion 143 performs sine correction for the whole image by using the reform start position acquired in Step S880. In this step, a sine correction method is the same as that used in Step S820. Although the line images are formed by the correction directed to several line images in Step S820, the whole image is corrected in this step. After the image is reformed in this manner, the processing returns to Step S240.

(Step S250)

In Step S250, the output portion 150 displays the reformed image of the retina, which is stored in the memory portion 130 in Step S240, on a monitor or the like. Further, the estimate value of the frequency and the reform start position, which are stored in the memory portion 130 in Steps S210 to S240, are stored in a database.

By the configuration described above, when the image of the retina is to be acquired by the adaptive optics SLO apparatus, the frequency of the resonance scanner can be estimated to form the image whose distortion resulting from the resonance scanner is corrected, without a special hardware configuration for specifying the scanner position.

Second Embodiment

In the first embodiment, there has been described the processing of evaluating the estimate value of the frequency of the resonance scanner by using the correlation coefficient and acquiring the frequency at which the correlation coefficient becomes the largest as the estimate value, to automatically reform the image.

According to a second embodiment of the present invention, the value of the frequency is changed while a user is observing the image.

Figure 11:
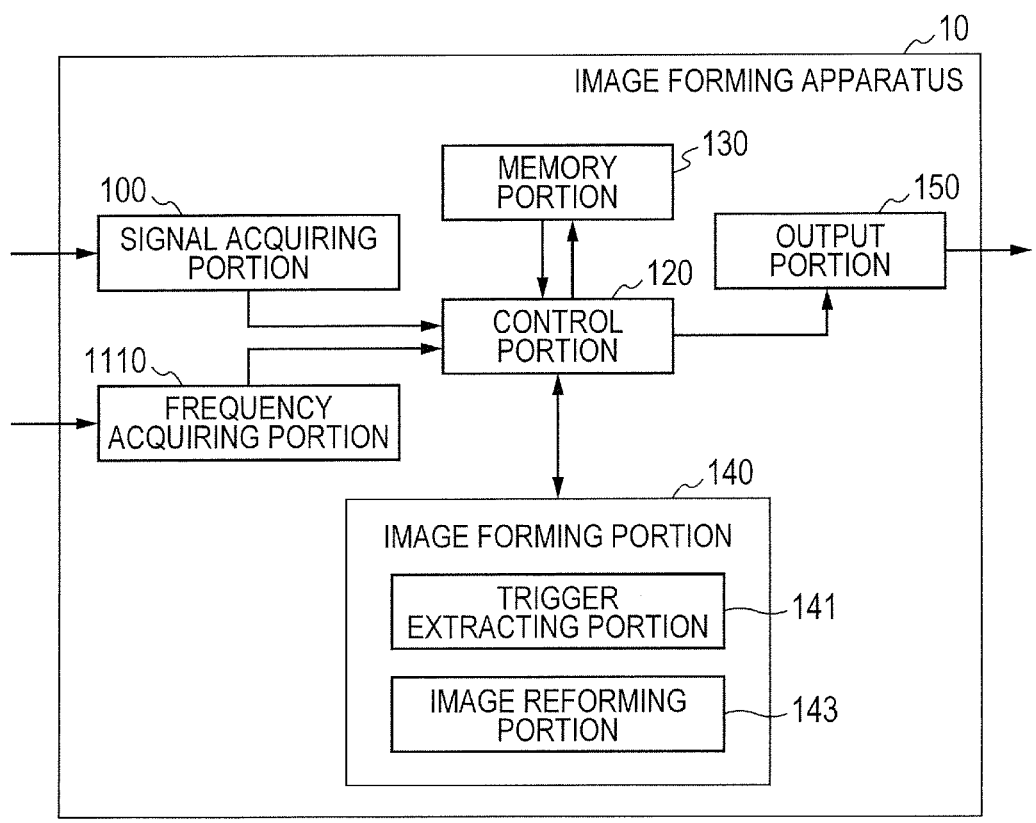
FIG. 11 is a diagram illustrating a functional configuration of an image forming apparatus according to a second embodiment of the present invention.

A functional configuration of the image forming apparatus 10 according to the second embodiment is illustrated in FIG. 11. The functional configurations of the signal acquiring portion 100, the control portion 120, the memory portion 130, and the output portion 150 are the same as those illustrated in FIG. 1, and therefore the description thereof is herein omitted. In the second embodiment, the image forming portion 140 includes only the trigger extracting portion 141 and the image reforming portion 143. Instead of the estimation of the frequency, which is performed by the frequency estimating portion 142 in the first embodiment, the image is reformed by using a third frequency which is a frequency input by the user in a frequency acquiring portion 1110 which is a frequency acquiring unit.

Referring to a flowchart of FIG. 12, a processing procedure of the image forming apparatus 10 according to the second embodiment is described. In the processing procedure, the processing in Steps S210, S220, and S240 is the same as that described in the first embodiment. Therefore, the description thereof is herein omitted.

(Step S1230)

In Step S1230, the image forming portion 140 sets an initial value of the frequency of the resonance scanner. In this step, the initial value is obtained by, for example, approximating the number of trigger signals for the resonance scanner, which are contained during the sampling for one image, as described above for Step S410. The thus acquired frequency is stored in the memory portion 130 through the control portion 120.

(Step S1250)

In Step S1250, the output portion 150 displays the reformed image of the retina, which is stored in the memory portion 130 in Step S240, and the frequency stored in the memory portion 130 in Step S1230, on the monitor or the like.

(Step S1260)

In Step S1260, the frequency acquiring portion 1110 determines whether or not the frequency is changed by the user for the frequency and the generated reformed image of the retina, which are displayed in Step S1250. When the frequency is not changed, the processing is terminated. When the frequency is changed, the processing proceeds to Step S1270.

(Step S1270)

In Step S1270, the frequency acquiring portion 1110 acquires the value of the frequency, which is input by the user, and stores the acquired value of the frequency in the memory portion 130 through the control portion 120. Thereafter, the processing returns to Step S240 where the image is reformed again based on the newly acquired frequency. Specifically, in the second embodiment, the frequency of the resonance scanner, which is determined based on the extracted trigger signal, or the frequency input by the user, is acquired by the frequency acquiring portion. Based on the acquired frequency, the image is reformed. In this embodiment, as the predetermined processing executed for the determination of the frequency, a frequency acquiring step for acquiring the frequency of the resonance scanner, which is input by the user, and an image reforming step for reforming the image based on the acquired frequency of the resonance scanner, are included.

By the configuration described above, when the image of the retina, which is acquired by the adaptive optics SLO apparatus, is to be formed, the frequency of the resonance scanner can be adjusted while the user is observing the image, thereby selecting an optimal frequency.

Another Embodiment

It should be understood that the object of the present invention can also be achieved with the following configuration. A software program code for implementing the functions of the above-mentioned embodiments is stored on a storage medium, and the storage medium is supplied to a system or an apparatus. Then, a computer (or CPU or MPU) of the system or the apparatus reads out and executes the program code stored on the storage medium.

Further, the present invention is not limited to the embodiments described above, which can be modified or changed variously within the scope of the present invention without deviating from the spirit thereof. For instance, the above-mentioned embodiments describe the case where the object to be inspected is an eye, but the present invention can be applied to an object to be inspected such as skin or organs other than the eye. In this case, the present invention includes an exemplary embodiment as medical equipment such as an endoscope other than an ophthalmic apparatus. Therefore, it is desired that the present invention be understood as an inspection apparatus such as an ophthalmic apparatus, and that the eye to be inspected be understood as an exemplary embodiment of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-288358, filed Dec. 28, 2012, which is hereby incorporated by reference herein in its entirety.

What is claimed is:

1. An image forming apparatus for forming an image of an object to be inspected using return light from the object to be inspected which is irradiated with measurement light via a scanner, the image forming apparatus comprising:
    a signal detecting unit for detecting signals output from the scanner which is set to scan the object to be inspected with the measurement light at a first frequency;
    a determining unit for determining a second frequency which is estimated to be used for the scanning by the scanner, by comparing a first correlation between the detected signals and signals obtained by shifting the detected signals by a cycle of the first frequency, with a second correlation between the detected signals and signals obtained by shifting the detected signals by a cycle of a different frequency different from the first frequency; and
    an image forming unit for forming the image of the object to be inspected using (1) the determined second frequency and (2) the return light from the object to be inspected which is irradiated with the measurement light via the scanner.

2. An image forming apparatus according to claim 1, wherein the determining unit determines, as the second frequency, a frequency between the first frequency and the different frequency, when it is determined whether or not a difference between the first correlation and the second correlation is equal to or smaller than a predetermined range and it is determined that the difference between the first correlation and the second correlation is equal to or smaller than the predetermined range.

3. An image forming apparatus according to claim 2, wherein the determining unit, (a) when it is determined that the difference between the first correlation and the second correlation is not equal to or smaller than the predetermined range, obtains a third correlation between the detected signals and signals obtained by shifting the detected signals by a cycle of a further frequency different from the first frequency and the different frequency, and changes the further frequency so that a difference between the second correlation and the third correlation is equal to or smaller than the predetermined range, and (b) determines, as the second frequency, a frequency between the different frequency and the further frequency, when it is determined that the difference between the second correlation and the third correlation is equal to or smaller than the predetermined range.

4. An image forming apparatus according to claim 1, wherein a correlation coefficient designating the first correlation and the second correlation comprises a Pearson's correlation coefficient.

5. An image forming apparatus according to claim 1, further comprising a light-receiving portion for generating an optical signal by receiving the return light from the object to be inspected irradiated with the measurement light via the scanner,
    wherein the image forming unit comprises:
    (a) a position associating unit for associating positions of pixels of the image and irradiated positions at which the object to be inspected is irradiated with the measurement light, using the determined second frequency; and
    (b) a line-image forming unit for forming a linear image using intensities of the optical signals acquired from the irradiated positions associated with the positions of pixels.

6. An image forming apparatus for forming an image of an object to be inspected using return light from the object to be inspected which is irradiated with measurement light via a scanner, the image forming apparatus comprising:
    a detecting unit for detecting signals output from the scanner which is set to scan the object to be inspected with the measurement light at a first frequency;
    an acquiring unit for acquiring one of a second frequency estimated to be used for the scanning by the scanner and a third frequency set for the scanning by the scanner, the second frequency being determined by comparing a first correlation between the detected signals and signals obtained by shifting the detected signals by a cycle of the first frequency, with a second correlation between the detected signals and signals obtained by shifting the detected signals by a cycle of a different frequency different from the first frequency; and
    an image forming unit for forming the image of the object to be inspected using (1) one of the second frequency and the third frequency and (2) the return light from the object to be inspected which is irradiated with the measurement light via the scanner.

7. An image forming method for forming an image of an object to be inspected using return light from the object to be inspected which is irradiated with measurement light via a scanner, the image forming method comprising:

detecting signals output from the scanner which is set to scan the object to be inspected with the measurement light at a first frequency;

determining a second frequency which is estimated to be used for the scanning by the scanner, by comparing a first correlation between the detected signals and signals obtained by shifting the detected signals by a cycle of the first frequency, with a second correlation between the detected signals and signals obtained by shifting the detected signals by a cycle of a different frequency different from the first frequency; and forming the image of the object to be inspected using (1) the determined second frequency and (2) the return light from the object to be inspected which is irradiated with the measurement light via the scanner.

8. An image forming method according to claim 7, wherein the determining comprises determining, as the second frequency, a frequency between the first frequency and the different frequency, when it is determined whether or not a difference between the first correlation and the second correlation is equal to or smaller than a predetermined range and it is determined that the difference between the first correlation and the second correlation is equal to or smaller than a predetermined range.

9. An image forming method according to claim 8, wherein the determining comprises:
obtaining, when it is determined that the difference between the first correlation and the second correlation is not equal to or smaller than the predetermined range, a third correlation between the detected signals and signals obtained by shifting the detected signals by a cycle of a further frequency different from the first frequency and the different frequency;

changing the further frequency so that a difference between the second correlation and the third correlation is equal to or smaller than the predetermined range; and determining, as the second frequency, a frequency between the different frequency and the further frequency, when it is determined that the difference between the second correlation and the third correlation is equal to or smaller than the predetermined range.

10. An image forming method according to claim 7, wherein a correlation coefficient designating the first correlation and the second correlation comprises a Pearson's correlation coefficient.

11. An image forming method according to claim 7, further comprising receiving reflected light of the measurement light by a light-receiving portion for respectively generating an optical signal by receiving the return light from the object to be inspected irradiated with the measurement light via the scanner,
wherein the forming comprises:
(a) associating positions of pixels of the image and irradiated positions at which the object to be inspected is irradiated with the measurement light, using the determined second frequency; and
(b) forming a linear image using intensities of the optical signals acquired from the irradiated positions associated with the positions of pixels.

12. An image forming method for forming an image of an object to be inspected using return light from the object to be inspected which is irradiated with measurement light via a scanner, the image forming method comprising:
detecting signals output from the scanner which is set to scan the object to be inspected with the measurement light at a first frequency;

acquiring one of a second frequency estimated to be used for the scanning by the scanner and a third frequency set for the scanning by the scanner, which is input by a user, the second frequency being determined by comparing a first correlation between the detected signals and signals obtained by shifting the detected signals by a cycle of the first frequency, with a second correlation between the detected signals and signals obtained by shifting the detected signals by a cycle of a different frequency different from the first frequency; and forming the image of the object to be inspected using (1) one of the second frequency and the third frequency and (2) the return light from the object to be inspected which is irradiated with the measurement light via the scanner.

13. A program for controlling a computer to perform each of the steps of the image forming method according to claim 7.

14. An ophthalmic apparatus for photographing an eye to be inspected using return light from the eye to be inspected which is irradiated with measurement light via a scanner, the ophthalmic apparatus comprising:
a signal detecting unit for detecting signals output from the scanner which is set to scan the eye to be inspected with the measurement light at a first frequency;
a determining unit for determining a second frequency which is estimated to be used for the scanning by the scanner, by comparing a first correlation between the detected signals and signals obtained by shifting the detected signals by one cycle of the first frequency, with a second correlation between the detected signals and signals obtained by shifting the detected signals by one cycle of a different frequency different from the first frequency; and
an image acquiring unit for acquiring the image of the eye to be inspected using (1) the determined second frequency and (2) the return light from the eye to be inspected which is irradiated with the measurement light via the scanner.

15. An ophthalmic apparatus for photographing an eye to be inspected using return light from the eye to be inspected which is irradiated with measurement light via a scanner, the ophthalmic apparatus comprising:
a detecting unit for detecting signals output from the scanner which is set to scan the eye to be inspected with the measurement light at a first frequency;
an acquiring unit for acquiring one of a second frequency estimated to be used for the scanning by the scanner and a third frequency set for the scanning by the scanner, which is input by a user, the second frequency being determined by comparing a first correlation between the detected signals and signals obtained by shifting the detected signals by a cycle of the first frequency, with a second correlation between the detected signals and signals obtained by shifting the detected signals by a cycle of a different frequency different from the first frequency; and
an image acquiring unit for acquiring the image of the eye to be inspected using (1) one of the second frequency and the third frequency and (2) the return light from the object to be inspected which is irradiated with the measurement light via the scanner.

16. An image forming apparatus according to claim 1, wherein the scanner is a resonance scanner.

17. An ophthalmic apparatus according to claim 14, wherein the scanner is a resonance scanner.

18. An image forming apparatus according to claim 16, further comprising a galvano scanner for scanning the measurement light on the object to be inspected in a direction different from a direction along which the measurement light is scanned by the resonance scanner,
    wherein the signal detecting unit detects the signals output from the resonance scanner by using as a reference a signal output from the galvano scanner.

19. An ophthalmic apparatus according to claim 17, further comprising a galvano scanner for scanning the measurement light on the eye to be inspected in a direction different from a direction along which the measurement light is scanned by the resonance scanner,
    wherein the signal detecting unit detects the signals output from the resonance scanner by using as a reference a signal output from the galvano scanner.

20. An image forming apparatus according to claim 5, wherein the image forming unit compares brightness difference in arrayed pixels in the linear image, and shifts the linear images so that a difference between the brightness differences in arrayed pixels in the linear images adjacent to another is equal to or less than a predetermined different value.

21. An image forming method according to claim 11, wherein the image is formed by comparing brightness difference in arrayed pixels in the linear image, and shifting the linear images so that a difference between the brightness differences in arrayed pixels in the linear images adjacent to another is equal to or less than a predetermined different value.

* * * * *